United States Patent [19]

Stevens, Jr. et al.

[11] Patent Number: 4,851,350

[45] Date of Patent: Jul. 25, 1989

[54] MICROBIAL DESULFURIZATION OF COAL

[75] Inventors: Stanley E. Stevens, Jr.; Wilella D. Burgess, both of Centre County, Pa.

[73] Assignee: The Standard Oil Company, Cleveland, Ohio

[21] Appl. No.: 21,402

[22] Filed: Mar. 4, 1987

[51] Int. Cl.[4] .............................. C12P 1/02; C12P 1/00
[52] U.S. Cl. .................................... 435/262; 435/264; 435/282
[58] Field of Search ......................... 435/282, 264, 262

[56] References Cited

U.S. PATENT DOCUMENTS

| | | |
|---|---|---|
| 2,829,964 | 4/1958 | Zimmerley et al. |
| 3,218,252 | 11/1965 | Glover et al. |
| 3,266,889 | 8/1966 | Duncan et al. |
| 3,305,353 | 2/1967 | Duncan et al. |
| 3,540,983 | 11/1970 | Rose et al. ............ 435/875 |
| 4,206,288 | 6/1980 | Detz et al. |
| 4,562,156 | 12/1985 | Isbister et al. |
| 4,659,670 | 4/1987 | Stevens et al. |

OTHER PUBLICATIONS

Technical Bulletin No. 1029, U.S. Dept. Agric., p. 38.
Lodder—The Yeasts (1971) North Holland Pub. Co., p. 267.
Sci. Amer. 247(2): 44–53 (Aug. 1982) Microbiological Mining.
Biotechnology News, vol. 2 (6) Aug. 15, 1982.
Kargi, Enzyme Microb. Technol., 1982 (Jan.) vol. 4, pp. 13–19.
*The Prokaryotes*, vol. 1, Edited by M. P. Starr et al. 1981, pp. 1023–1036, *The Genera Thiobacillus* and *Thiomicrospira*, Kuenen et al.
Starkey, Ind. Eng. Chem. (1956) vol. 48, No. 9, pp. 1429–1437.

*Primary Examiner*—Sam Rosen
*Attorney, Agent, or Firm*—Michael F. Esposito; David J. Untener; Larry W. Evans

[57] ABSTRACT

A process for the microbial desulfurization of the coal utilizing *Hansenula sydowiorum, Hansenula ciferrii, Hansenula lynferdii,* and/or *Cryptococcus albidus.*

9 Claims, No Drawings

MICROBIAL DESULFURIZATION OF COAL

BACKGROUND OF THE INVENTION

The present invention relates to microorganisms which are capable of reproducible reduction of sulfur in coal and, more particularly, to a process for the microbial desulfurization of coal.

An increasing awareness of the need to utilize alternative energy sources has prompted renewed interest in obtaining satisfactory methods of cleanly and efficiently burning coal. A substantial disadvantage long felt by the industry is the deleterious effect upon the environment which results from th products of coal combustion. Emission of sulfur oxides into the atmosphere has long been of particular concern.

Many grades of coal and petroleum contain large quantities of sulfur compounds which form corrosive air and water pollutant products during combustion. The presence of sulfur in coal appears in three basic forms; as sulfates, pyrite and organic sulfur. Of the three, sulfates are the least significant, comprising less than 0.5 weight percent of the coal. Pyritic and organic sulfur, however, may each constitute as much as 3.5 weight percent of the coal or from 40 to 60% of the total sulfur content, respectively. Thus, it is apparent that removal of an effective portion of this sulfur content prior to coal combustion would substantially reduce the emission of sulfur oxides into the atmosphere.

Commercial attention has primarily been focused upon the removal of pyritic sulfur which has been relatively easy to facilitate. These processes include numerous physical and mechanical techniques such as heavy media separation, selective agglomeration, floatation, jigging, magnetic separation, leaching and hydrosulfurization. However, the removal of organic sulfur has not met with the same success. By organic sulfur, is meant, that sulfur which is chemically bound within the coal matrix. Organic sulfur is present in four major forms. These are mercaptans or thiols, sulfide, disulfide and aromatic ring sulfur as exemplified by the thiophene system. Since organic sulfur is chemically bound within the coal molecule, effective removal techniques employed must be essentially chemical or biological.

Processes for the biological removal of sulfur from coal are known in the art but until recently have only been successful for the oxidation of pyritic sulfur. For example, such a process is disclosed by U.S. Pat. No. 4,206,288 which employs an iron and sulfur oxidizing microorganism selected from the *Thiobacillus ferroxidans* group. Microorganisms chosen from this acidophilic group have long been known to have the capability of oxidizing the sulfide and ferrous iron in ores containing sulfide minerals. For example, U.S. Pat. No. 2,829,964 discloses a process for leaching metals such as copper from mixed oxide and sulfide copper ores utilizing an acid solution containing these bacteria.

Oxidation of the sulfide and/or ferrous iron to sulfate and ferric iron can be utilized to release numerous other metals from the mineral lattice. These include iron, nickel, zinc, molybdenum, copper, uranium and aluminum. Other processes which employ *Thiobacillus ferroxidans* for these known capabilities are disclosed, for example, in U.S. Pat. Nos. 3,218,252, 3,226,899 and 3,305,353. None of the aforementioned references, however, show any effect on the reduction of organic sulfur, although, as indicated, pyritic sulfur has been oxidized and thereby removed from coal with some success.

Methods for the removal of organic sulfur from coal are known but are quite expensive and particularly inefficient, usually employing extreme conditions such as high pressure and high temperature. Typically, the coal product treated by these processes is substantially altered and often may not be utilized for its intended purpose.

Processes for the removal of organic sulfur compounds by microbial treatment have been recently investigated. For example, U.S. Pat. No. 4,562,156 discloses a mutant microorganism Pseudomonas sp. CBI having a registry number ATCC 39381 to be effective in removing organic sulfur compounds from coal. Copending U.S. application Ser. No. 495,657, filed May 18, 1983, discloses a mixed culture of microorganisms comprising one or more of Pseudomonas, Acinetobacter, Azotobacter, and Flavobacteria having a registry number ATCC 39327 which is extremely effective in the removal of organic sulfur from coal.

Removal of organic sulfur compounds by microbial treatment has many advantages. Since high temperature, high pressure or corrosion resistant equipment are not required for the biological process, inexpensive construction materials can be used leading to low capital costs. Moreover, biological treatment is not likely to significantly alter the structure and the composition of the coal or to substantially reduce the BTU value of the coal.

SUMMARY OF THE INVENTION

It is therefore one object of the present invention to provide microorganisms capable of reproducible sulfur metabolism.

Another object of this invention is to provide microorganisms capable of reproducible sulfur reduction in carbonaceous solids, such as coal.

A further object of the present invention is to provide a process for the microbial desulfurization of carbonaceous solids, such as coal.

A still further object of this invention is to provide a continuous process for the microbial desulfurization of coal.

Still another object of the present invention is to provide a process for the microbial desulfurization of coal which provides coal having a reduced sulfur content including reduced pyritic sulfur content and particularly reduced organic sulfur content.

These and other objects are accomplished herein by a process for the microbial desulfurization of carbonaceous solids, said process comprising contacting an aqueous carbonaceous solids slurry with a microorganism selected from the group consisting of *Hansenula sydowiorum, Hansenula ciferrii, Hansenula lynferdii, Cryptococcus albidus* and mixtures thereof.

DETAILED DESCRIPTION OF THE INVENTION

The microbial desulfurization process of the present invention is broadly applicable to the treatment of various types of sulfur containing coal. In particular, coals which can be desulfurized in accordance with the present process include anthracite, bituminous, subbituminous, mine tailings, fines, lignite and the like. Other finely divided solid carbonaceous solids, such as coke may also benefit from the present process. Preferably, the coal subjected to the present desulfurization process is in particulate form.

Thus, in carrying out a preferred embodiment of the present invention, raw mined coal is first reduced to a particle size smaller than about 200 mesh. While it is not necessary for the present process, the particulate coal may then be beneficiated. A particularly preferred beneficiation process is disclosed in U.S. Pat. No. 4,412,843. The beneficiated (or unbeneficiated) coal particles are then formed into a slurry with water in such a manner that the solids concentration in the slurry is between about 2% and about 40% by weight.

In accordance with the present invention, the aqueous coal slurry is then innoculated with a microorganism culture selected from *Hansenula sydowiorum, Hansenula ciferrii, Hansenula lynferdii,* and *Cryptococcus albidus*. A nutrient medium is generally added to the aqueous coal slurry in order to provide a source of metabolites and an alternative carbon source to the coal matrix itself. A typical nutrient medium for this purpose comprises ammonium chloride or ammonuim hydroxide, calcium chloride, potassium phosphate, magnesium chloride and glucose. Care is taken to avoid sources of sulfate sulfur so as to encourage the microorganisms to consume the sulfur contained in the coal matrix. The temperature at which the desulfurization process is carried out is generally between about 20°–25° C. and the pH is generally maintained between from about 6 to about 8, i.e., essentially neutral pH conditions, preferably from about 7 to about 7.4.

The microorganisms employed in the present process are known in the art. *Hansenula sydowiorum, Hansenula ciferrii* and *Hansenula lynferdii* are known eukaryotes (yeasts), while *Cryptococcus albidus* is a known fungus. These microorganisms are found naturally inhabiting the soil. Notwithstanding, the microorganisms of the present invention can be grown or cultured by methods which are well known in the art. In general, the microorganisms used in the present process can be obtained from the enrichment from normal soil by in-situ application of organic sulfur compounds and the subsequent isolation, for example, by selective pressure of an antibiotic. More particularly, the microorganisms useful in the present invention can be grown in-situ in soil which is enriched with organic sulfur compounds including cystine, cysteine, methionine, thiophene, thianapthene, beta-mercaptoethanol, methionine sulfoximine, methionine sulfoxide, dibenzothiophene and the like. Other ingredients used in the enrichment can include organic compounds such as biphenyl and the like which are added to the site of microorganisms to induce a phenomena known as cometabolism, i.e., organisms which naturally cleave biphenyl will also cleave dibenzothiophene and thus are environmentally pressure selected for their capability of metabolizing sulfur. The desired microorganism can be isolated by dilution plating, selective pressure of an antibiotic such an actidione or by other conventional methods.

In another embodiment of the present invention, the microorganism cultures of the present invention can be implemented subsequently or concurrently in a batch, continuous or semicontinuous process for the desulfurization of the coal. For example, after proper incubation, the culture is innoculated into a reaction vessel. Concurrently, an aqueous slurry of particulate coal and a nutrient medium is continuously provided under continuous stirring and aeration, whereby the coal is subjected to the sulfur reduction activity of the culture mixture, while maintaining essentially neutral pH conditions. Sulfur reduced coal and the inhibitory end products of organic sulfur metabolism are continuously removed from the reaction vessel. The nutrient medium utilized is 0.01% $KH_2PO_4$, 0.01% $MgCl_2$, 0.01% $CaCl_2.2H_2O$. Additional nutrients selected from the group of compounds consisting of glucose, succinic acid, butyric acid, and lactic acid may also be added. When these additional compounds are employed, they are generally buffered, such as, for example, by NaOH, to maintain the requisite pH level hereinbefore discussed.

Analysis of the coal treated by the present process, reveals that the present process can provide an average of up to about 46% reduction of the total sulfur content of the coal which for the most part is a reduction in the organic sulfur content.

It has been found that the period of time that the coal is maintained in contact with the active microorganisms medium, i.e., residence time, varies depending upon the specific conditions under which the desulfurization is carried out. Generally, a residence time of from about 16 hrs. to about 72 hrs. is required. Thus, in order to carry out the process in a continuous cycle, the slurry is removed from the reaction vessel and fresh slurry is added at a rate which corresponds to a residence time equal to that given above. At the conclusion of the contact period, solid desulfurized coal is recovered by separating the coal from the liquid phase of the slurry, using well known techniques such as filtering or settling. While not wishing to be bound, it is believed that the especially good desulfurization results achieved herein using Hansenula spp. (*ciferrii* and *sydowiorum*) are in part caused by an in-situ production by these microorganisms of a surfactant-like extracellular matrix material which enables these microorganisms to bind very tightly to the surface to the coal facilitating sulfur removal.

The following examples are illustrative of the practice of the invention.

EXAMPLE 1

Media was prepared with ammonium chloride, ammonium hydroxide, calcium chloride, potassium phosphate, magnesium chloride, glucose, biphenyl and thianthrene. The medium was inoculated with *Hansenula cifferri* and a 10% coal slurry. Samples were taken at various time intervals. Sulfur reductions were as follows:

| Time (hrs.) | % S reduction |
| --- | --- |
| 0 | — |
| 16 | 16.5 |
| 23 | 16.2 |
| 40 | 22.3 |
| 64 | 23.9 |
| 71 | 21.8 |

EXAMPLE 2

To eliminate some of the variability caused by the heterogenous nature of coal, experimentation was carried out involving the substitution of a model compound for the coal. The compound chosen for the experimentation was dibenzothiophene (DBT) which is reported to be the most similar to the types of organic sulfur found in coal. *Hansenula sydowiorum* was grown at 27° C., 7.4 pH in culture with DBT in the presence of ammonuim chloride or ammonuim hydroxide, calcium chloride, potassium phosphate, magnesium chloride and glucose. Samples were taken at 24 hour intervals for two days. The DBT remaining in the medium was extracted using anhydrous ethyl ether and the DBT concentration was measured by means of a gas chromtograph with flame ionization detector. The results show that *Hansenula sydowiorum* is capable of removing more than 60% of the sulfur in DBT in 48 hours.

EXAMPLE 3

A crude extract was isolated from each of *Hansenula ciferrii* and *Hansenula sydowiorum*. This was accomplished by growing up 20 liters of cells, spinning the cells out by means of a Sharples centrifuge, separating the cell material from the mother liquor, and concentrating the mother liquor by means of rotoevaporation thereby obtaining the extract. The crude extract from *Hansenula ciferrii* was further purified by ether extraction. The resulting extracts, when added to the coal medium which was innoculated with the corresponding organism, caused a noticeable increase in the rate of desulfurization.

While the invention has been described with reference to certain preferred embodiments, those skilled in the art will realize that changes and modifications may be made thereto without departing from the full and intended scope of the appended claims.

We claim:

1. A process for the microbial desulfurization of solid carbonaceous solids, said process comprising subjecting an aqueous slurry of carbonaceous solids to the desulfurizing action of microorganisms selected from the group consisting of *Hansenula sydowiorum, Hansenula ciferrii, Hansenula lynferdii, Cryptococcus albidus* and mixtures thereof.

2. The process of claim 1 carried out at essentially neutral pH conditions.

3. The process of claim 1 carried out in the presence of a nutrient medium for said microorganisms.

4. The process of claim 3 wherein said nutrient medium is selected from the group consisting of ammonuim chloride, ammonuim hydroxide, calcium chloride, potassium phosphate, magnesium chloride, glucose and mixtures thereof.

5. The process of claim 2 wherein said essentially neutral pH is in the range of from about 6 to about 8.

6. The process of claim 5 wherein the temperature is maintained at about 20° to about 25° C.

7. The process of claim 1 wherein said carbonaceous solids is coal.

8. A process for the microbial desulfurization of coal comprising subjecting an aqueous coal slurry to the desulfurizing action of microorganisms selected from the group consisting of *Hansenula sydowiorum, Hansenula ciferrii, Hansenula lynferdii, Cryptococcus albidus* and mixtures thereof in the presence of a nutrient medium for said microorganisms at essentially neutral pH conditions and room temperature.

9. The process of claim 8 carried out continuously by continuously feeding said aqueous coal slurry and said nutrient medium to said microorganisms.

* * * * *